United States Patent
Shi et al.

(10) Patent No.: US 11,820,763 B2
(45) Date of Patent: **\*Nov. 21, 2023**

(54) BROMOPHENOL-PYRAZOLINE COMPOUND AND SYNTHESIS METHOD AND USE THEREOF

(71) Applicant: Lead High Technology (QingDao) Co., Ltd, Shandong (CN)

(72) Inventors: Dayong Shi, Qingdao (CN); Xiangqian Li, Qingdao (CN); Xin Wang, Qingdao (CN); Jinbo Yang, Qingdao (CN)

(73) Assignee: Lead High Technology (QingDao) Co., Ltd, Qingdao (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/375,635

(22) Filed: Jul. 14, 2021

(65) Prior Publication Data

US 2022/0041585 A1  Feb. 10, 2022

(30) Foreign Application Priority Data

Aug. 4, 2020  (CN) .......................... 202010773200.6

(51) Int. Cl.
*C07D 231/06* (2006.01)
*C07D 417/04* (2006.01)
*A61P 31/14* (2006.01)

(52) U.S. Cl.
CPC ............ *C07D 417/04* (2013.01); *A61P 31/14* (2018.01); *C07D 231/06* (2013.01)

(58) Field of Classification Search
CPC ......................... C07D 231/06; C07D 417/04
See application file for complete search history.

(56) References Cited

U.S. PATENT DOCUMENTS

| 8,865,754 B2 * | 10/2014 | Esposito | .............. C07D 409/14 |
| | | | 548/235 |
| 2022/0041585 A1 | 2/2022 | Shi et al. | |
| 2022/0193036 A1 * | 6/2022 | Shi | .............. A61K 31/415 |
| 2022/0363644 A1 | 11/2022 | Shi et al. | |

FOREIGN PATENT DOCUMENTS

CN  106496123 A  *  3/2017  ........... C07D 231/06

OTHER PUBLICATIONS

Chemical Abstracts Registry No. 2524718-75-8, indexed in the Registry file on STN CAS Online Nov. 20, 2020. (Year: 2020).*
Chemical Abstracts Registry No. 2524719-17-1, indexed in the Registry file on STN CAS Online Nov. 20, 2020. (Year: 2020).*
Chemical Abstracts Registry No. 1428324-84-8, indexed in the Registry file on STN CAS Online Apr. 15, 2013. (Year: 2013).*
Chemical Abstracts Registry No. 857183-15-4, indexed in the Registry file on STN CAS Online Jul. 27, 2005. (Year: 2005).*
PubChem CID 155672551, National Center for Biotechnology Information. PubChem Compound Summary for CID 155672551. https://pubchem.ncbi.nlm.nih.gov/compound/155672551. Accessed Mar. 31, 2023, create date Feb. 21, 2021. (Year: 2021).*
A machine generated English translation of CN 106496123 A, 2017 (Pan et al.). (Year: 2017).*

* cited by examiner

*Primary Examiner* — Laura L Stockton

(57) ABSTRACT

The present invention relates to a compound, and in particular to a bromophenol-pyrazoline compound and a synthesis method and use thereof. The bromophenol-pyrazoline compound is represented by a general structural formula below:

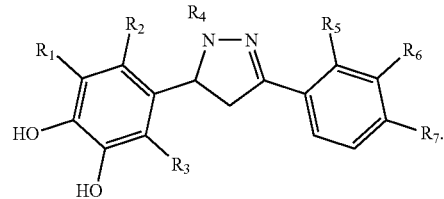

The bromophenol-pyrazoline compound provided in the present invention has efficient inhibitory activity against the main protease $M^{pro}$, and interferes with the replication of coronavirus in cells, indicating that the compound has the effect of treating coronavirus pneumonia and thus has a broad prospect of application in the preparation of drugs for treating coronavirus pneumonia.

6 Claims, 3 Drawing Sheets

$IC_{50}=3.09 \pm 0.94 (uM)$

BROMOPHENOL-PYRAZOLINE COMPOUND AND SYNTHESIS METHOD AND USE THEREOF

TECHNICAL FIELD

The present invention relates to a compound, and particularly to a bromophenol-pyrazoline compound and a synthesis method and use thereof.

BACKGROUND

The new coronavirus is an enveloped positive-sense type B single-stranded RNA coronavirus. During the life cycle of the coronavirus, all replications and transcriptions are performed by the polyprotein replicases ppla and pplab. Before becoming a mature functional protein, ppla and ppab need to be hydrolyzed in the presence of the host's cellular enzyme, and they are active only after hydrolysis. This important polyproteolytic process in the life cycle of the virus is completed by the main protease ($M^{pro}$) encoded by the virus, and is essential for processing polyproteins translated from viral RNA. Therefore, inhibiting the activity of this enzyme can effectively suppress viral replication Countries around the world are speeding up the development of novel coronavirus pneumonia vaccines, and some vaccines have entered the clinical trial stage. However, there are multiple serotypes of coronaviruses, which can produce repeated infections; and complete immunization is difficult to achieve. At present, there is no high-potent drugs for treating COVID-19 available on the market. The broad-spectrum antiviral drugs or traditional Chinese medicines are widely used clinically to treat various symptoms, but the therapeutic effect is undesirable.

The global pandemic of new coronavirus pneumonia has brought great challenges to the living environment of the entire human race, severely affected the human life and production activities, and caused immeasurable losses to the development of human society. Therefore, it is imminent to develop a targeted drug useful for the treatment of coronavirus pneumonia by inhibiting the activity of the main protease $M^{pro}$ and interfering with the replication of coronavirus.

SUMMARY OF THE INVENTION

An object of the present invention is to provide a bromophenol-pyrazoline compound. It is found through research that the bromophenol-pyrazoline compound has efficient inhibitory activity against the main protease $M^{pro}$, and has the ability to inhibit the replication of coronavirus in cells, and thus is useful as a target drug to treat new coronavirus pneumonia.

To achieve the object of the present invention, the following technical solution is adopted in the present invention. A bromophenol-pyrazoline compound is provided, which is represented by a general structural formula below:

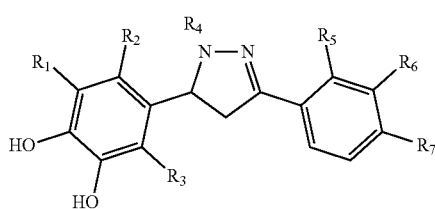

where $R_1$, $R_2$, and $R_3$ are respectively any one selected from H, Br, and OH;

$R_4$ is any one selected from H, CHO, $COCH_3$, $COCH_2CH_3$, $COCH_2CH_2CH_3$, $COOCH_3$, $COOCH_2CH_3$, Ph, $CH_2Ph$, $CONH_2$, $CSNH_2$,

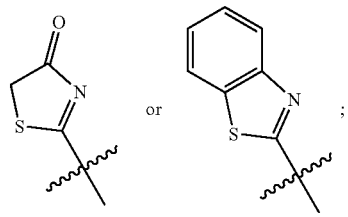 [SMILES: *C1=NC(=O)CS1 ; *c1nc2ccccc2s1]

and $R_5$, $R_6$, and $R_7$ are respectively any one selected from H, Br, $NO_2$, OH, $CH_3$, $OCH_3$ or

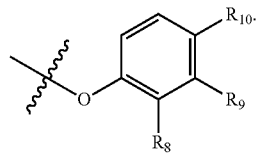

According to a preferred embodiment of the present invention, $R_8$, $R_9$, and $R_{10}$ in

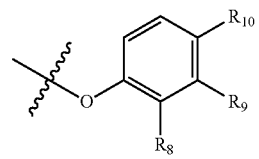

are respectively any one selected from H, methyl, ethyl, methoxy, ethoxy, isopropyl, and t-butyl.

The present invention further provides a method for synthesizing the bromophenol-pyrazoline compound, which comprises

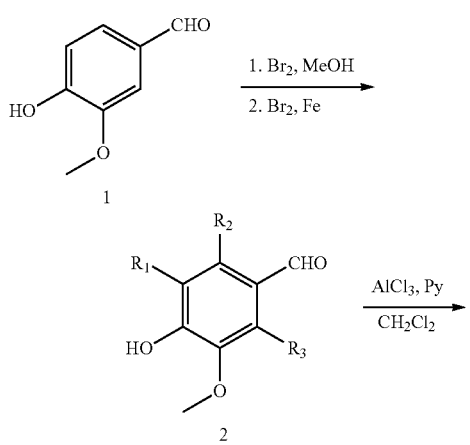

brominating vanillin (1) with bromine to produce bromovanillin (2), then removing the methyl group in the presence of AlCl₃ and pyridine to obtain brominated 3,4-dihydroxybenzaldehyde (3); reacting the compound 3 with a substituted acetophenone (4) in the presence of SOCl₂, to produce the intermediate product chalcone (5); and cyclizing the compound (5) with a hydrazine in an ethanol solution heated to reflux, to obtain the target product bromophenol-pyrazoline (6);

where $R_1$, $R_2$, and $R_3$ are respectively any one selected from H, Br, and OH;

$R_4$ is any one selected from H, CHO, COCH₃, COCH₂CH₃, COCH₂CH₂CH₃, COOCH₃, COOCH₂CH₃, Ph, CH₂Ph, CONH₂, CSNH₂, and $R_5$, $R_6$, and $R_7$ are respectively any one selected from H, Br, NO₂, OH, CH₃, OCH₃ or Further preferably, $R_8$, $R_9$, and $R_{10}$ in are respectively any one selected from H, methyl, ethyl, methoxy, ethoxy, isopropyl, and t-butyl.

The present invention further provides use of the compound. Since the compound can inhibit the activity of the main protease $M^{pro}$, it can be prepared into an antiviral preparation for the treatment of coronavirus pneumonia.

Further, the present invention also provides a drug for the treatment of coronavirus pneumonia, which comprises an effective dose of one or a mixture of two or more of the bromophenol-pyrazoline compounds as described above.

One or a mixture of two or more of the bromophenol-pyrazoline compounds is mixed with a pharmaceutically acceptable drug carrier and prepared into, for example, tablets, capsules, oral liquids, granules, pills or injections for the prevention and/or treatment of coronavirus pneumonia.

Beneficial effects of the present invention: The present invention provides a bromophenol-pyrazoline compound and a method for synthesizing the same. The compound has high-efficiency inhibitory activity against main protease $M^{pro}$ and can interfere with the replication of coronavirus in cells, suggesting that the compound has the efficacy of treating coronavirus pneumonia, and has broad prospect of application in the preparation of drugs for treating coronavirus pneumonia.

BRIEF DESCRIPTION OF ACCOMPANYING DRAWINGS

FIGS. 1(a) to 1(d) shows the results of determining the inhibitory activity of the compounds 6a-6g provided in the examples of the present invention on the main protease $M^{pro}$ of COVID-19, in which the effect of various compounds at various concentrations on the $M^{pro}$ activity is determined, and the half maximum inhibitory concentration (IC₅₀) is determined by nonlinear regression.

DETAILED DESCRIPTION

Figure 1A:
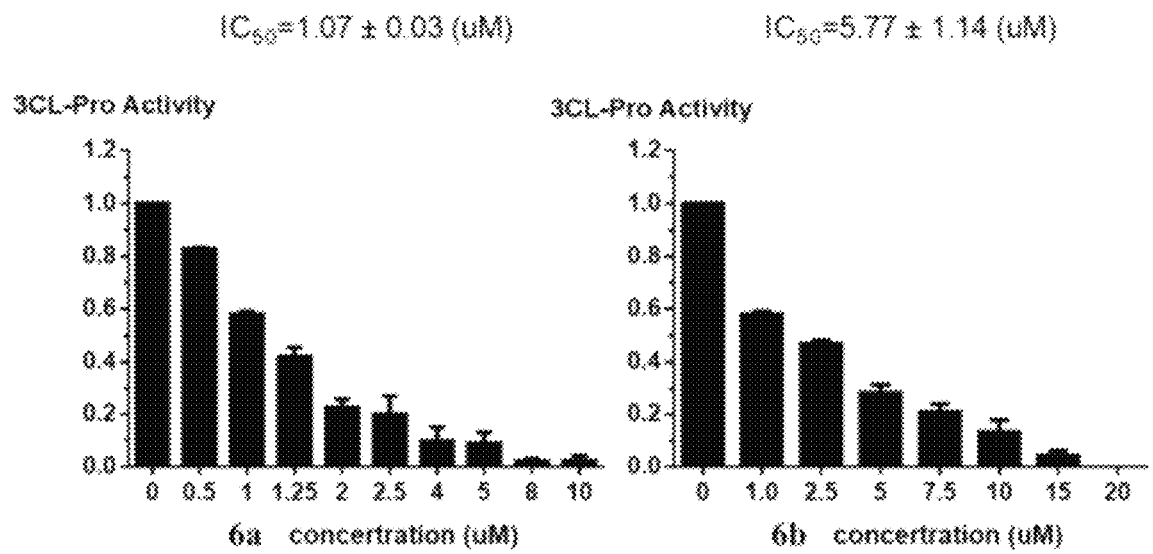
Figure 1B:
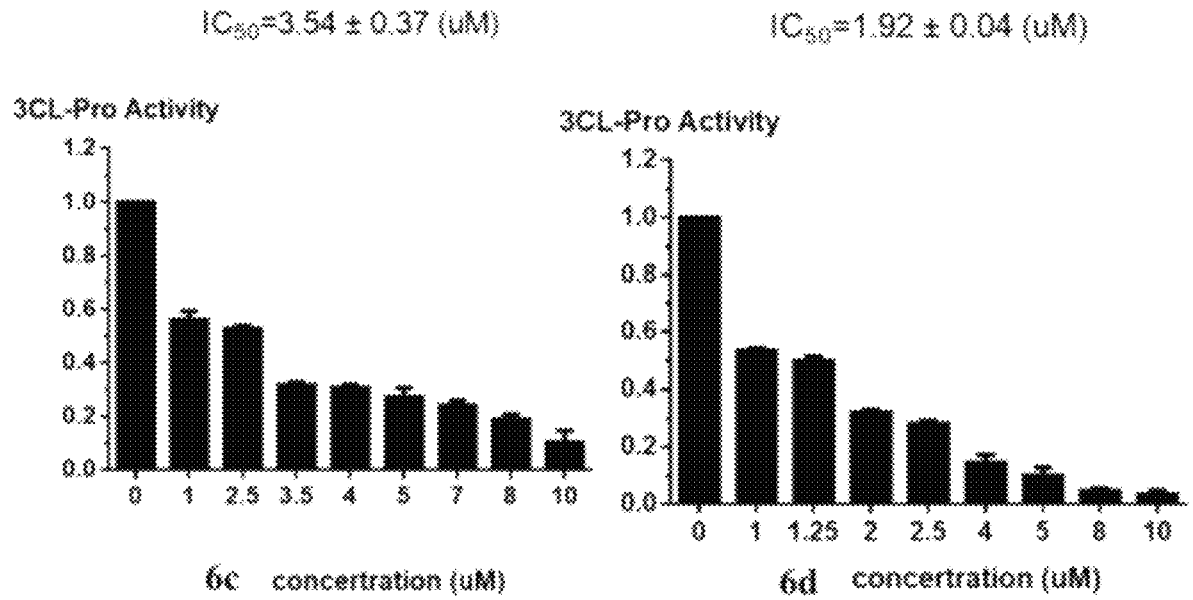
Figure 1C:
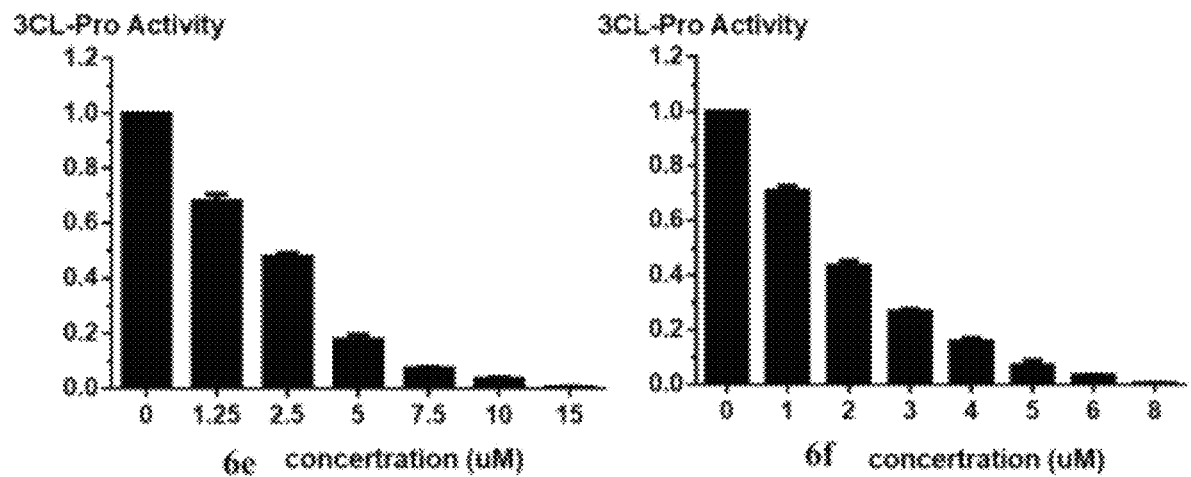
Figure 1D:
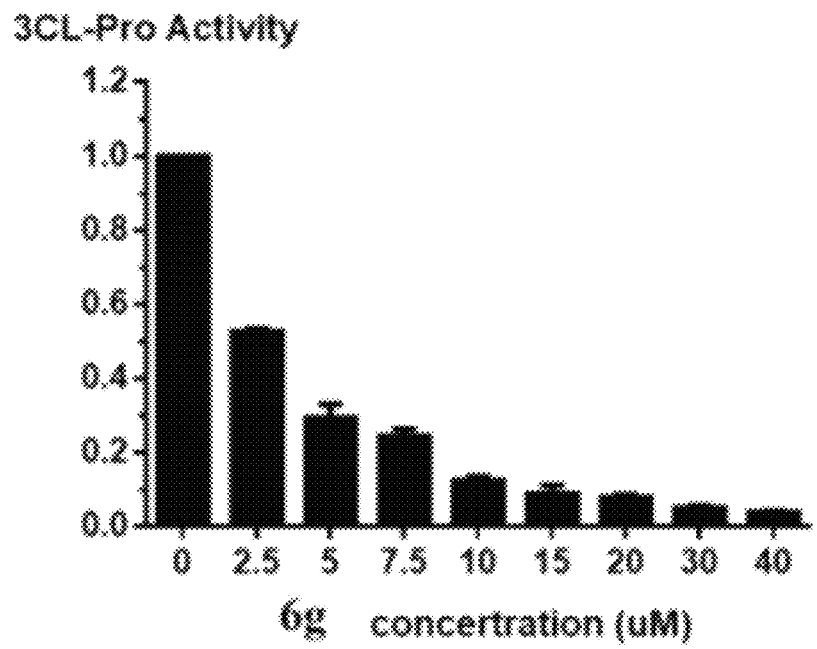

To facilitate the understanding of the present invention, the present invention will be described in more detail below with reference to the accompanying drawings and specific embodiments. The preferred embodiments of the present invention are shown in the drawings. However, the present invention can be implemented in many different forms and is not limited to the embodiments described in this specification. On the contrary, the purpose of providing these embodiments is to make the understanding of the disclosure of the present invention more thorough and comprehensive.

EXAMPLE 1

Synthesis and Characterization of 3,4-dibromo-5-(3-(4-(4-ethoxyphenoxy)phenyl)-4,5-dihydro-1H-pyrazol-5-yl)-1,2-dihydroxybenzene (6a)

(1) Synthesis Route and Specific Steps

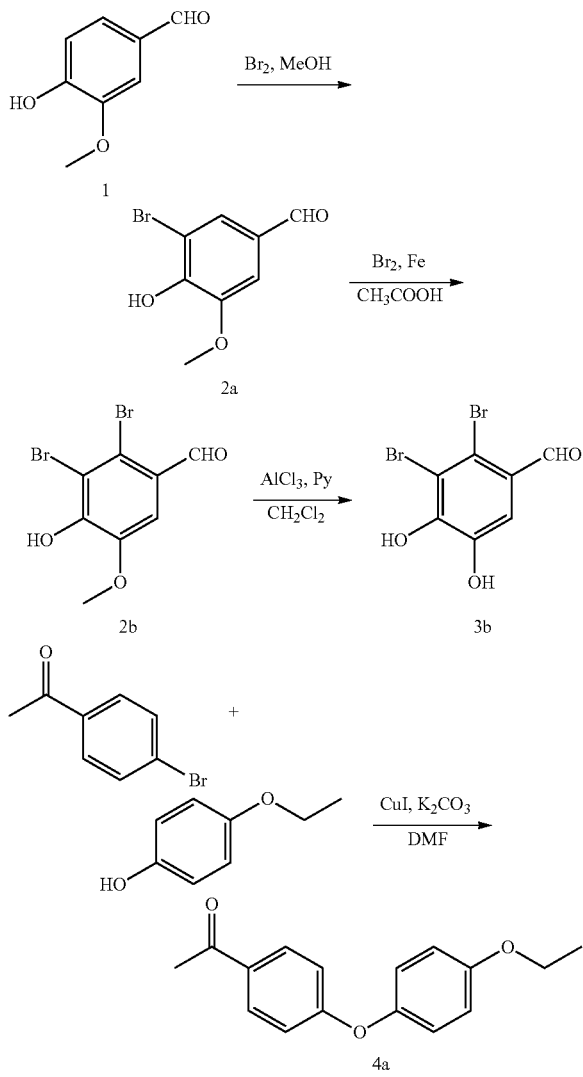

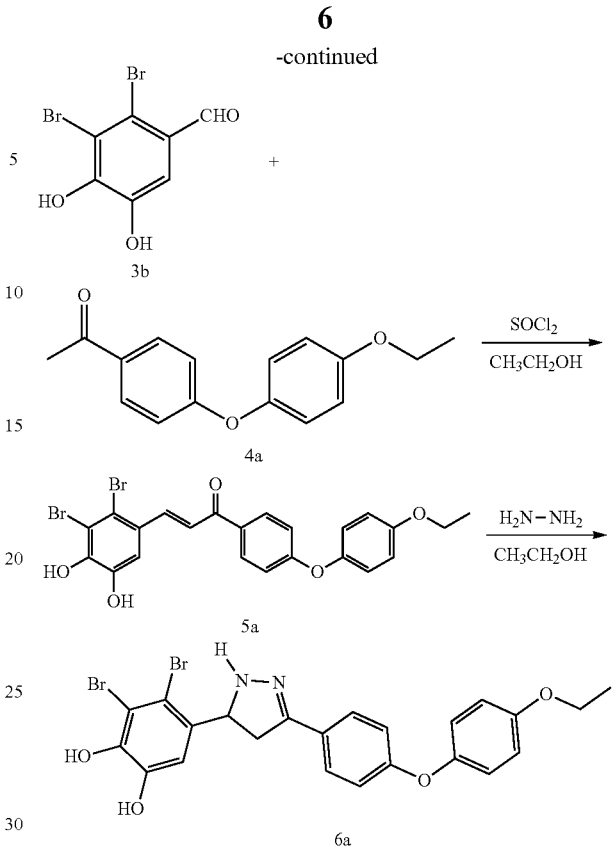

Vanillin (15.2 g, 0.1 mol) was added to dichloromethane (100 mL), and stirred until uniform. A solution of bromine (5.6 mL, 16.0 g, 0.1 mol) in methanol (10 mL) was added dropwise in an ice bath with stirring. The reaction was continued at room temperature for 2 hrs, and then cooled to 0° C. Ice-cold water (50 mL) was added dropwise, and a precipitate was formed, which was filtered, washed with ice-cold water, and dried, to obtain 5-bromo-vanillin as a white solid (21 g) (2a, yield 92%, mp 160-162° C.).

5-bromo-vanillin (21 g, 2a, 0.09 mol) was added to acetic acid (100 mL), and a solution of bromine (10.26 mL, 0.2 mol) in acetic acid (15 mL) was added dropwise with stirring at normal temperature. Reduced iron powder (0.1 g) was added, and the reaction was carried out under reflux for 2 hrs. After cooling to room temperature, the precipitate was filtered. The solid was recrystallized in ethyl acetate, to obtain 5,6-dibromovanillin as a white needle-like crystal (25.2 g) (2b, yield 81.8%, mp 230-233° C.).

5,6-dibromovanillin (15.5 g, 2b, 0.05 mol) was added to dichloromethane (100 mL), and stirred until uniform. Solid $AlCl_3$ (10 g, 0.075 mol) was carefully added. A solution of pyridine (23 g, 0.290 mol) in $CH_2Cl_2$ (10 mL) was slowly added dropwise in an ice bath with stirring. After that, the reaction was carried out under reflux for 24 hrs. The reaction solution was cooled, and adjusted to pH<3 with 1 M hydrochloric acid. The aqueous phase was separated, extracted with ethyl acetate, dried, and evaporated to dryness, to obtain 2,3-dibromo-4,5-dihydroxybenzaldehyde as a pale yellow solid (13.5 g) (3b, 91.5%, mp: 206-208° C.).

4-bromobenzaldehyde (19.9 g, 0.1 mol), 4-ethoxyphenol (16.56 g, 0.12 mol), $K_2CO_3$ (16.56 g, 0.12 mol), and CuI (1.9 g, 0.01 mol) were weighed and added to DMF (200 mL), heated to 140° C., and reacted for 8 hrs with stirring. After cooling, the reaction solution was added with water (200 mL), extracted with ethyl acetate, dried, evaporated to dryness, and separated by column chromatography on silica gel with petroleum ether:ethyl acetate=30:1 as a mobile phase, to obtain a white flaky solid (13.1 g, 51.1%), which is the intermediate product 4-(4-ethoxyphenoxy)acetophenone (4a).

2,3-dibromo-4,5-dihydroxybenzaldehyde (3b) (2.96 g, 0.01 mol) and 4-(4-ethoxyphenoxy)acetophenone (4a) (2.56 g, 0.01 mol) were weighed, and added to ethanol (20 mL). A solution of $SOCl_2$ (0.5 mL) in ethanol (5 mL) was added dropwise with stirring, and then stirred overnight at normal temperature. Water (10 mL) was added, and allowed to stand for 1 hrs. The solid was filtered off, washed with water and ethanol, and dried, to obtain (E)-3-(2,3-dibromo-4,5-dihydroxyphenyl)-1-(4-(4-ethoxyphenoxy)phenyl)prop-2-en-1-one as a yellow solid (5a) (3.1 g, 58%).

Compound (5a) (267 mg, 0.5 mmol) was weighed and dissolved in ethanol (3 mL). 3 drops of hydrazine hydrate (concentration: 85%) were added with stirring, and the solution turned dark red. Then, the reaction solution was heated to reflux for 2 hrs, cooled, and allowed to stand overnight. A white solid was precipitated out, ultrasonicated, filtered, and washed with water and ethanol to obtain the final product 3,4-dibromo-5-(3-(4-(4-ethoxyphenoxy)phenyl)-4,5-dihydro-1H-pyrazol-5-yl)benzene-1,2-dihydroxy (6a) (128 mg, yield 46.7%).

(2) Characterization of Compound $^1$H NMR (500 M Hz, DMSO-d6) δ 10.05 (s, 1H), 9.49 (s, 1H), 7.57 (d, J=8.6 Hz, 2H), 7.48 (s, 1H), 7.06 (s, 1H), 7.01-6.96 (m, 2H), 6.94 (d, J=9.0 Hz, 2H), 6.88 (dd, J=5.6, 3.0 Hz, 2H), 4.97 (t, J=10.2 Hz, 1H), 3.99 (q, J=6.9 Hz, 2H), 3.48 (dd, J=16.6, 10.9 Hz, 1H), 2.60 (dd, J=16.5, 9.5 Hz, 1H), 1.31 (t, J=6.9 Hz, 3H).

$^{13}$C NMR (126M Hz, DMSO-d6) δ 158.57 (s), 155.52 (s), 149.33 (s), 148.12 (s), 145.75 (s), 144.14 (s), 134.84 (s), 128.04 (s), 127.60 (s), 121.34 (s), 117.54 (s), 116.05 (s), 113.59 (s), 113.43 (s), 113.21 (s), 109.81 (s), 64.07 (s), 63.81 (s), 63.08 (s), 15.14 (s).

EXAMPLE 2

Synthesis and Characterization of 5-(2,3-dibromo-4,5-dihydroxyphenyl)-3-(4-(4-ethoxyphenoxy)phenyl)-4,5-dihydro-1H-pyrazol-1- carboxaldehyde (6b)

(1) Synthesis Route and Specific Steps

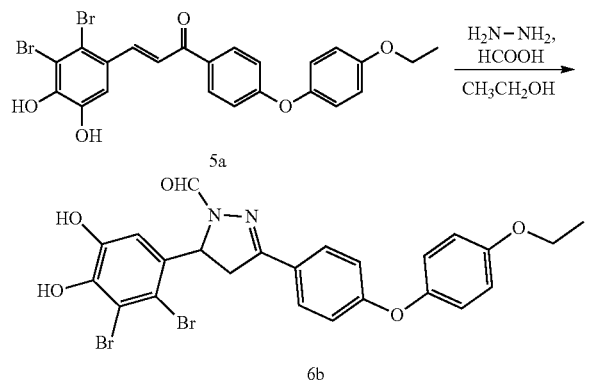

Compound (5a) (267 mg, 0.5 mmol) was weighed and dissolved in a mixed solution of ethanol (3 mL) and formic acid (1 mL), and then 5 drops of hydrazine hydrate (concentration: 85%) was added with stirring. The reaction solution was heated to reflux for 2 hrs, cooled, and allowed to stand overnight. A white solid was precipitated out, ultrasonicated, filtered, and washed with water and ethanol to obtain the final product 5-(2,3-dibromo-4,5-dihydroxyphenyl)-3-(4-(4-ethoxyphenoxy)phenyl)-4,5-dihydro-1H-pyrazol-1- carboxaldehyde (6b) (176 mg, yield 61.1%).

(2) Characterization of Compound $^1$H NMR (500M Hz, DMSO-d6) δ 8.94 (s, 1H), 7.75 (d, J=8.3 Hz, 2H), 7.04 (d, J=8.9 Hz, 2H), 6.97 (dd, J=13.6, 8.8 Hz, 4H), 6.53 (s, 1H), 5.63 (dd, J=11.4, 3.8 Hz, 1H), 4.03-4.00 (m, 2H), 3.91 (dd, J=17.8, 11.8 Hz, 1H), 3.04 (dd, J=17.9, 4.3 Hz, 1H), 1.33 (t, J=6.9 Hz, 3H).

$^{13}$C NMR (126M Hz, DMSO-d6) δ 160.69 (s), 159.89 (s), 156.30 (s), 155.92 (s), 148.69 (s), 146.19 (s), 129.20 (s), 125.24 (s), 121.83 (s), 117.39 (s), 116.19 (s), 112.34 (s), 63.87 (s), 59.73 (s), 42.15 (s), 15.16 (s).

EXAMPLE 3

Synthesis and Characterization of 5-(2,3-dibromo-4,5-dihydroxyphenyl)-3-(4-(4-ethoxyphenoxy)phenyl)-4,5-dihydro-1H-1-acetyl pyrazole (6c)

(1) Synthesis Route and Specific Steps

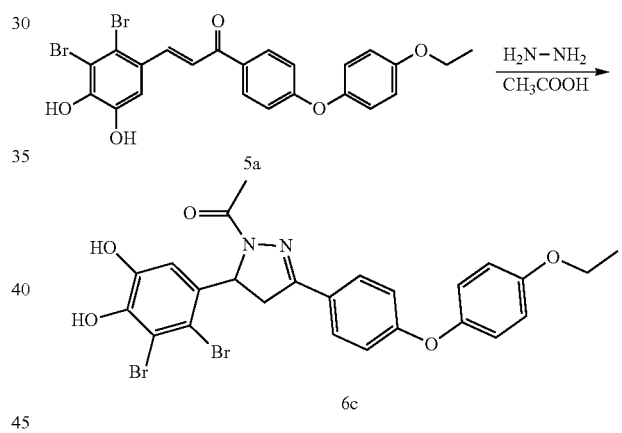

Compound (5a) (267 mg, 0.5 mmol) was weighed and dissolved in acetic acid (4 mL), and then 5 drops of hydrazine hydrate (concentration: 85%) was added with stirring. The reaction solution was heated to reflux for 2 hrs, cooled, and allowed to stand overnight. A white solid was precipitated out, ultrasonicated, filtered, and washed with water and ethanol to obtain the final product 5-(2,3-dibromo-4,5-dihydroxyphenyl)-3-(4-(4-ethoxyphenoxy)phenyl)-4,5-dihydro-1H-1-acetyl pyrazole (6c) (121 mg, yield 41.1%).

(2) Characterization of Compound $^1$H NMR (500M Hz, DMSO-d6) δ 9.97 (s, 1H), 9.54 (s, 1H), 7.73 (d, J=8.8 Hz, 2H), 7.01 (d, J=9.0 Hz, 2H), 6.98-6.91 (m, 4H), 6.46 (s, 1H), 5.61 (d, J=7.8 Hz, 1H), 4.05-3.98 (m, 2H), 3.89-3.82 (m, 1H), 2.95 (dd, J=17.9, 4.0 Hz, 1H), 2.31 (s, 3H), 1.31 (t, J=7.0 Hz, 3H).

$^{13}$C NMR (126M Hz, DMSO-d6) δ 167.56 (s), 160.39 (s), 155.80 (s), 154.41 (s), 148.79 (s), 145.96 (s), 144.29 (s), 133.22 (s), 129.05 (s), 125.62 (s), 121.63 (s), 117.45 (s), 116.15 (s), 113.99 (s), 112.15 (s), 63.84 (s), 22.11 (s), 15.13 (s).

EXAMPLE 4

Synthesis and Characterization of 2-(5-(2,3-dibromo-4,5-dihydroxyphenyl)-3-(4-(4-ethoxyphenoxy)phenyl)-4,5-dihydro-1H-pyrazol-1- substituted) thiazol-4 (5H)one (6d)

(1) Synthesis Route and Specific Steps

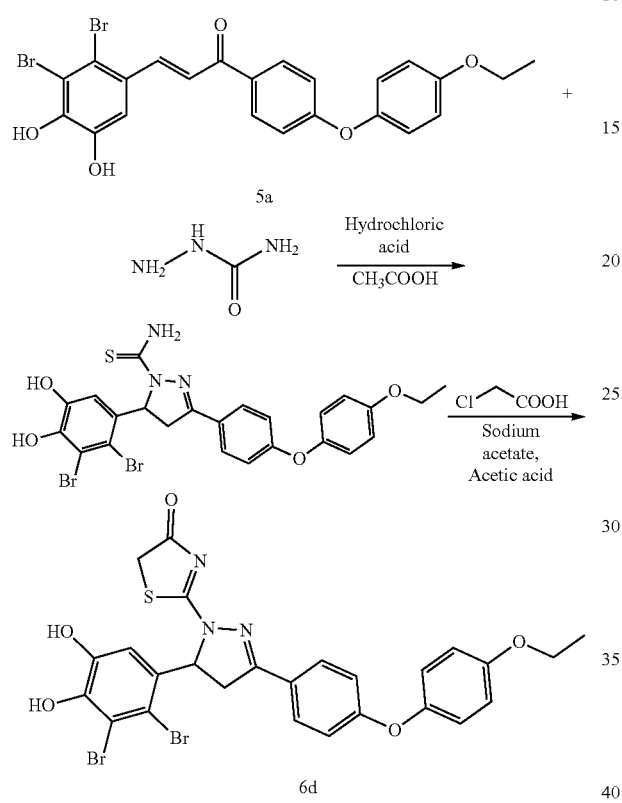

Compound (5a) (267 mg, 0.5 mmol) was weighed and dissolved in acetic acid (4 mL), and then thiosemicarbazide (54.6 mg, 0.6 mmol) and 1 drop of concentrated hydrochloric acid were added in sequence, then heated to 120° C., and reacted for 4 hrs at this temperature with stirring. The reaction solution was cooled, added with water (2 mL), and allowed to stand for 1 hr. The solid was filtered out, washed with water and then with ethanol, and dried to obtain the intermediate product 5-(2,3-dibromo-4,5-dihydroxyphenyl)-3-(4-(4-ethoxyphenoxy)phenyl)-4,5-dihydro-1H-pyrazol-1-carbothioamide.

The intermediate product (231 mg) obtained in the previous step was added to acetic acid (2 mL), and then chloroacetic acid (37.8 mg, 0.4 mmol) and sodium acetate (49.2 mg, 0.6 mmol) were added. The system was heated to 100° C., and reacted for 4 hrs. The reaction solution was cooled, added with water (1 mL), and allowed to stand for 1 hr. The solid was filtered out, washed with water and then with ethanol, and dried to obtain 2-(5-(2,3-dibromo-4,5-dihydroxyphenyl)-3-(4-(4-ethoxyphenoxy)phenyl)-4,5-dihydro-1H-pyrazol-1-substituted) thiazol-4 (5H) one as a white solid (6d) (137 mg, yield 42.3%).

(2) Characterization of Compound $^1$H NMR (500M Hz, DMSO-d6) δ 9.95 (s, 1H), 9.56 (s, 1H), 7.80 (d, J=8.7 Hz, 2H), 7.00 (d, J=8.0 Hz, 2H), 6.66 (d, J=8.1 Hz, 2H), 6.55 (d, J=8.7 Hz, 2H), 6.48 (s, 1H), 5.56 (d, J=7.8 Hz, 1H), 4.00 (m, 3H), 3.88 (s, 2H), 3.32-3.26 (m, 1H), 1.31 (t, J=6.9 Hz, 3H).

$^{13}$C NMR (126M Hz, DMSO-d6) δ 187.24 (s), 177.25 (s), 161.30 (s), 160.53 (s), 155.94 (s), 148.54 (s), 145.88 (s), 145.56 (s), 131.88 (s), 129.80 (s), 124.41 (s), 121.78 (s), 117.51 (s), 117.27 (s), 116.14 (s), 113.15 (s), 63.86 (s), 43.92 (s), 15.13 (s).

EXAMPLE 5

Synthesis and Characterization of 5-(3-bromo-4,5-dihydroxyphenyl)-3-(4-methoxyphenyl)-4,5-dihydro-1H-pyrazol-1-carbothioamide (6e)

(1) Synthesis Route and Specific Steps

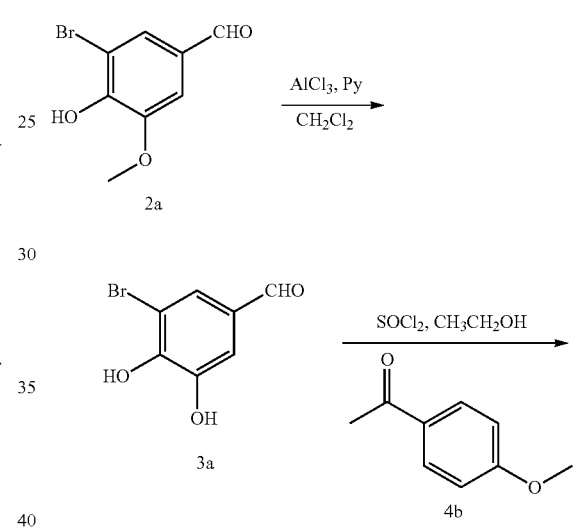

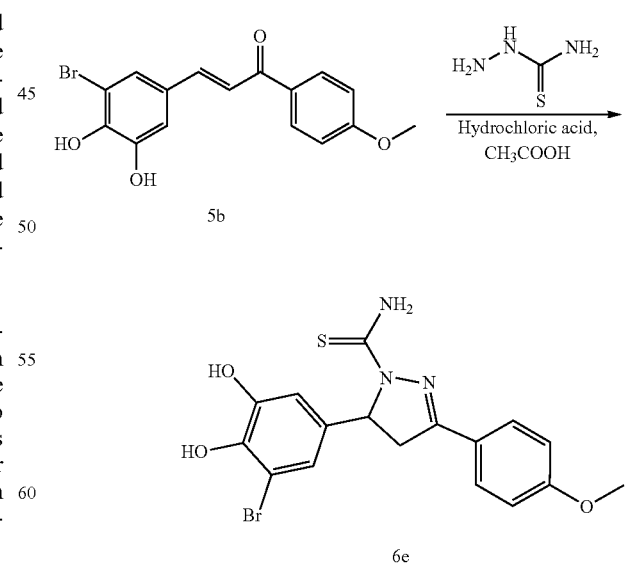

5-bromovanillin (11.6 g, 2a, 0.05 mol) was added to dichloromethane (100 mL), and stirred until uniform. Solid AlCl$_3$ (10 g, 0.075 mol) was carefully added. A solution of pyridine (23 g, 0.290 mol) in $CH_2Cl_2$ (10 mL) was slowly added dropwise in an ice bath with stirring. After that, the reaction was carried out under reflux for 24 hrs. The reaction solution was cooled, and adjusted to pH<3 with 1 M hydrochloric acid. The aqueous phase was separated, extracted with ethyl acetate, dried, and evaporated to dryness, to obtain 3-bromo-4,5-dihydroxybenzaldehyde as a pale yellow solid (9.8 g, 3a, 90.2%, mp:227-228° C.).

3-bromo-4,5-dihydroxybenzaldehyde (3a) (2.16 g, 0.01 mol) and 4-methoxyacetophenone (4b) (1.5 g, 0.01 mol) were weighed and added to ethanol (20 mL). A solution of $SOCl_2$ (0.5 mL) in ethanol (5 mL) was added dropwise with stirring. After that, the reaction solution was stirred overnight at normal temperature, added with water (10 mL), and allowed to stand for 1 hr. The solid was filtered out, washed with water and then with ethanol, and dried to obtain the intermediate product chalcone as a yellow solid (5b) (2.0 g, yield 57.5%).

Compound (5b) (175 mg, 0.5 mmol) was weighed and dissolved in acetic acid (4 mL), and then thiosemicarbazide (54.6 mg, 0.6 mmol) and 1 drop of concentrated hydrochloric acid were added in sequence, then heated to 120° C., and reacted for 4 hrs at this temperature with stirring. The reaction solution was cooled, added with water (2 mL), and allowed to stand for 1 hr. The solid was filtered out, washed with water and then with ethanol, and dried to obtain 5-(3-bromo-4,5-dihydroxyphenyl)-3-(4-methoxyphenyl)-4,5-dihydro-1H-pyrazol-1-carbothioamide as a white solid (6e) (130 mg, yield 61.6%).

(2) Characterization of Compound $^1$H NMR (500M Hz, DMSO-d6) δ 9.95 (s, 1H), 9.41 (s, 1H), 8.01 (s, 1H), 7.85 (s, 1H), 7.75 (d, J=8.8 Hz, 2H), 6.92 (d, J=8.8 Hz, 2H), 6.35 (s, 1H), 5.94 (d, J=11.1 Hz, 1H), 3.85-3.80 (m, 1H), 3.73 (s, 3H), 2.93 (dd, J=17.9, 3.0 Hz, 1H).

$^{13}$C NMR (126M Hz, DMSO-d6) δ 175.97 (s), 161.70 (s), 155.51 (s), 145.89 (s), 144.14 (s), 134.18 (s), 129.42 (s), 123.72 (s), 114.60 (s), 111.91 (s), 64.20 (s), 55.86 (s), 41.99 (s).

EXAMPLE 6

Synthesis and Characterization of 5-(3,4-dihydroxyphenyl)-3-(4-(4-ethoxyphenoxy)phenyl)-4,5-dihydro-1H-pyrazol-1-carbothioamide (6f)

(1) Synthesis Route and Specific Steps

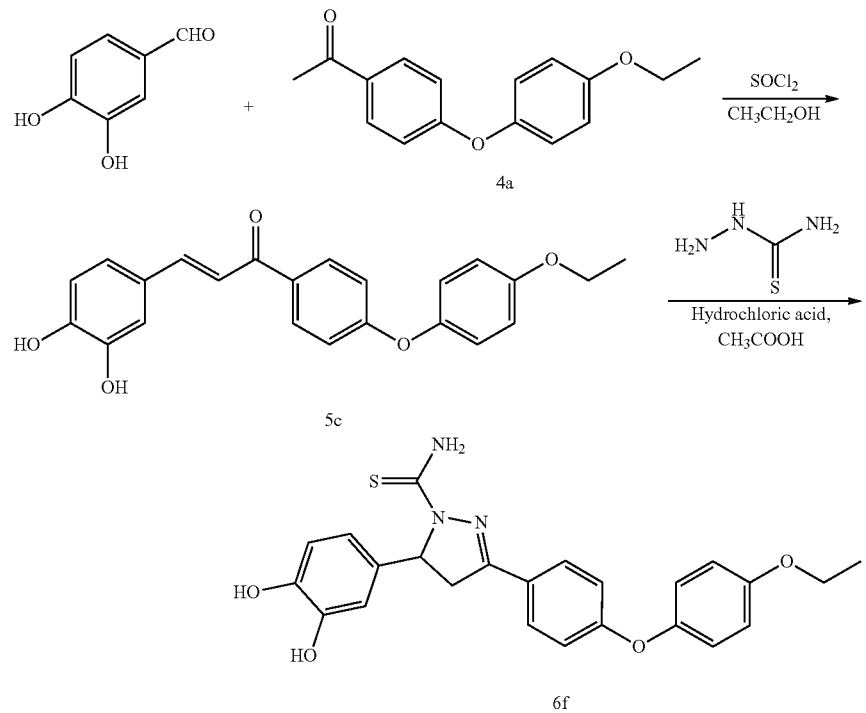

4,5-dihydroxybenzaldehyde (1.38 g, 0.01 mol) and 4-(4-ethoxyphenoxy)acetophenone (4a) (2.56 g, 0.01 mol) were weighed and added to ethanol (20 mL). A solution (5 mL) of 10% $SOCl_2$ in ethanol was added dropwise with stirring. After that, the reaction solution was stirred overnight at normal temperature, added with water (10 mL), and allowed to stand for 1 hr. The solid was filtered out, washed with water and then with ethanol, and dried to obtain the intermediate product chalcone as a yellow solid (5c) (2.6 g, yield 69.1%).

Compound (5c) (168 mg, 0.5 mmol) was weighed and dissolved in acetic acid (4 mL), and then thiosemicarbazide (54.6 mg, 0.6 mmol) and 1 drop of concentrated hydrochloric acid were added in sequence, then heated to 120° C., and reacted for 4 hrs at this temperature with stirring. The reaction solution was cooled, added with water (2 mL), and allowed to stand for 1 hr. The solid was filtered out, washed with water and then with ethanol, and dried to obtain 5-(3,4-dihydroxyphenyl)-3-(4-(4-ethoxyphenoxy)phenyl)-4,5-dihydro-1H-pyrazol-1-carbothioamide as a white solid (6f) (140 mg, yield 31.2%).

(2) Characterization of Compound $^1$H NMR (500M Hz, DMSO-d6) δ 8.85 (s, 1H), 8.73 (s, 1H), 7.89 (s, 1H), 7.83 (d, J=8.8 Hz, 2H), 7.74 (s, 1H), 7.06-6.98 (m, 2H), 6.94 (dd, J=11.0, 9.0 Hz, 4H), 6.61 (d, J=8.1 Hz, 1H), 6.47 (d, J=2.0 Hz, 1H), 6.39 (dd, J=8.1, 2.0 Hz, 1H), 5.70 (dd, J=11.1, 2.8 Hz, 1H), 4.00 (q, J=6.9 Hz, 2H), 3.76 (dd, J=17.9, 11.2 Hz, 1H), 3.02 (dd, J=17.8, 2.9 Hz, 1H), 1.31 (t, J=7.0 Hz, 3H).

$^{13}$C NMR (126M Hz, DMSO-d6) δ 176.11 (s), 160.51 (s), 155.79 (s), 155.04 (s), 148.78 (s), 145.55 (s), 144.70 (s), 134.49 (s), 129.47 (s), 125.69 (s), 121.64 (s), 117.36 (s), 116.80 (s), 116.12 (s), 115.86 (s), 112.97 (s), 63.83 (s), 62.89 (s), 43.01 (s), 40.45 (s), 15.13 (s).

EXAMPLE 7

Synthesis and Characterization of methyl 5-(4,5-dihydroxyphenyl)-3-(4-(4-ethoxyphenoxy)phenyl)-4,5-dihydro-1H-pyrazol-1-carboxylate (6g)

(1) Synthesis Route and Specific Steps

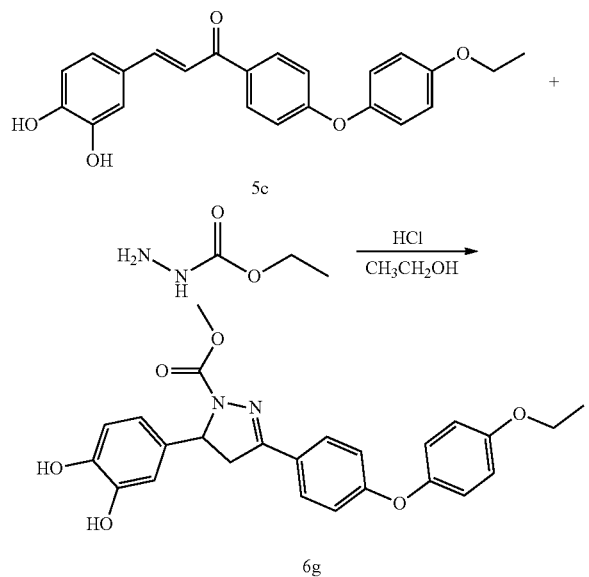

Compound (5c) (188 mg, 0.5 mmol) was weighed and dissolved in ethanol (4 mL). Ethyl carbazate (104 mg, 1.0 mmol), and 1 drop of concentrated hydrochloric acid were added in sequence, and reacted under reflux for 4 hrs. The reaction solution was cooled, and allowed to stand overnight. A white solid was precipitated, filtered out, washed with water and then with ethanol, and dried to obtain methyl 5-(4,5-dihydroxyphenyl)-3-(4-(4-ethoxyphenoxy)phenyl)-4,5-dihydro-1H-pyrazol-1-carboxylate (6g) (162 mg, yield 62.3%).

(2) Characterization of Compound $^1$H NMR (500M Hz, DMSO-d6) δ 8.92 (s, 1H), 8.80 (s, 1H), 7.70 (d, J=8.7 Hz, 2H), 7.02 (d, J=9.0 Hz, 2H), 6.94 (dd, J=11.4, 9.0 Hz, 4H), 6.64 (d, J=8.1 Hz, 1H), 6.53 (d, J=1.6 Hz, 1H), 6.44 (dd, J=8.1, 1.6 Hz, 1H), 5.22 (dd, J=11.6, 4.1 Hz, 1H), 4.00 (q, J=6.9 Hz, 2H), 3.72 (dd, J=17.8, 11.7 Hz, 1H), 3.60 (s, H), 3.02 (dd, J=17.8, 4.1 Hz, 1H), 1.31 (t, J=6.9 Hz, 3H).

$^{13}$C NMR (126M Hz, DMSO-d6) δ 160.18 (s), 155.79 (s), 153.66 (s), 152.90 (s), 148.80 (s), 145.81 (s), 145.09 (s), 134.14 (s), 128.90 (s), 125.96 (s), 121.70 (s), 117.38 (s), 116.88 (s), 116.05 (s), 112.88 (s), 63.83 (s), 60.97 (s), 52.84 (s), 15.13 (s).

EXAMPLE 8

Inhibitory Activity of Bromophenol-pyrazoline Compounds Against the Target $M^{pro}$ Protease of Novel Coronavirus (1) Experimental Materials:

The recombinant plasmid containing the $M^{pro}$ protease gene was synthesized by Wuhan AtaGenix Biotechnology Co., Ltd., the Ni Beads were purchased from Smart Lifescience, the multifunctional microplate reader was SpectraMax i3 from Molecular Device, the 96-well black plate was purchased from Corning, and other commonly used reagents were purchased from Sigma.

(2) Experimental Methods:

a. Expression and Purification of Recombinant $M^{pro}$ Protease.

The recombinant plasmid (pET28a (+)) containing $M^{pro}$ derived from SARS-CoV-2 was transformed into E. coli strain BL21 (codonplus), and then the strain was allowed to grow in LB or 2× YT medium to an OD600 of 0.6-0.8. Then 0.1 Mm isopropyl-1-thio-bD-galactoside (IPTG) was added, and the strain was allowed to grow at 15° C. for additional 24 hrs for low-temperature induction of expression. About 8-15 g of wet bacteria was harvested from 1 L of medium. The bacteria were re-suspended in a lysis buffer added at a ratio of 1:5, and the bacterial cells were disrupted by ultrasonic or high-pressure disruption. After centrifugation, the supernatant was purified by affinity chromatography on Ni Beads according to the manufacturer's instructions, and the protein purity was verified by SDS-PAGE.

b. Test of Inhibitory Activity of Bromophenol-pyrazoline Compounds Against $M^{pro}$ Protease.

660 μL of DMSO was added to a tube containing 1 mg of a substrate to give a final concentration of the substrate of 1 mM. After shaking in the dark at room temperature for 10 min, the solution was aliquoted in 20 μL/tube for use, and the remaining solution was stored at −20° C. 20 μL of 1 mM substrate was taken and diluted by adding 2 mL of a buffer (20 mM Sodium Phosphate Buffer, pH 6.8), and shaken on a shaker in the dark at room temperature for 5 min. $M^{pro}$ was removed from the freezer, thawed at room temperature for 5 min, and diluted with a buffer to 97 nM. 50 μL of the diluted $M^{pro}$ and 1 μL of various concentrations of diluted compounds of Examples 1-6 were added to each well of a 96-well plate. 50 μL of the diluted substrate was taken by a multi-channel pipette, and quickly added to the 96-well plate to react immediately. The plate was read immediately on a multifunctional microplate reader at an excitation wavelength of 320 nm and an emission wavelength of 405 nm. One measurement was made every 45 sec for consecutive 10 min. The slope in a linear interval was taken as V0 and the $IC_{50}$ of the compounds was calculated.

(3) Experimental Results:

a. Expression and Purification of High-Purity $M^{pro}$ Protease

A large amount of $M^{pro}$ protease was obtained by affinity chromatography on Ni Beads, and the purity was higher than 95%, as identified by SDS-PAGE, so the product can be used for subsequent enzyme activity test.

b. Test Results of Inhibitory Activity of Bromophenol-pyrazoline Compounds Against $M^{pro}$ Protease As shown in FIGS. 1(a) to 1(d), the bromophenol-pyrazoline compounds (6a-6g) have a significant inhibitory effect on $M^{pro}$ protease, and thus have a good prospect of application for the treatment of COVID-19 and other coronavirus induced pneumonia.

EXAMPLE 9

Bromophenol-pyrazoline Compounds Interfere with Virus Replication in Cells

In order to further confirm the results of enzyme inhibition in vitro, whether the bromophenol-pyrazoline compounds can prevent COVID-19 virus replication in Vero E6 cells infected with clinical isolates of COVID-19 virus was evaluated in the present invention.

Specific operations: The pre-seeded Vero E6 cells ($5\times10^4$ cells/well) were pre-treated for 1 hr with various concentrations of bromophenol-pyrazoline compounds to be tested, and then infected for 2 hrs by adding COVID-19 virus (with an MOI of 0.05). Then, the mixture of the virus and compound was removed, and the cells were further incubated in a fresh medium containing the bromophenol-pyrazoline compound. After 24 hrs, the cell supernatant was collected, and the vRNA in the supernatant was analyzed by qRT-PCR.

Figure 2:
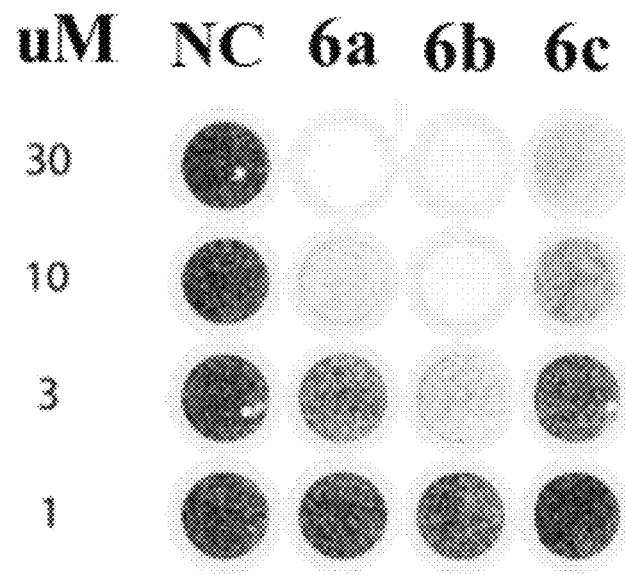
FIG. 2 shows the results of determining the inhibition of the compounds 6a-6c provided in the examples of the present invention on virus replication in cells, in which the supernatant of Vero E6 cells 72 hrs after infection with COVID-19 viruses is analyzed by qRT-PCR, and the effect of the compounds at various concentrations on viral RNA replication is evaluated.
Figure 3:
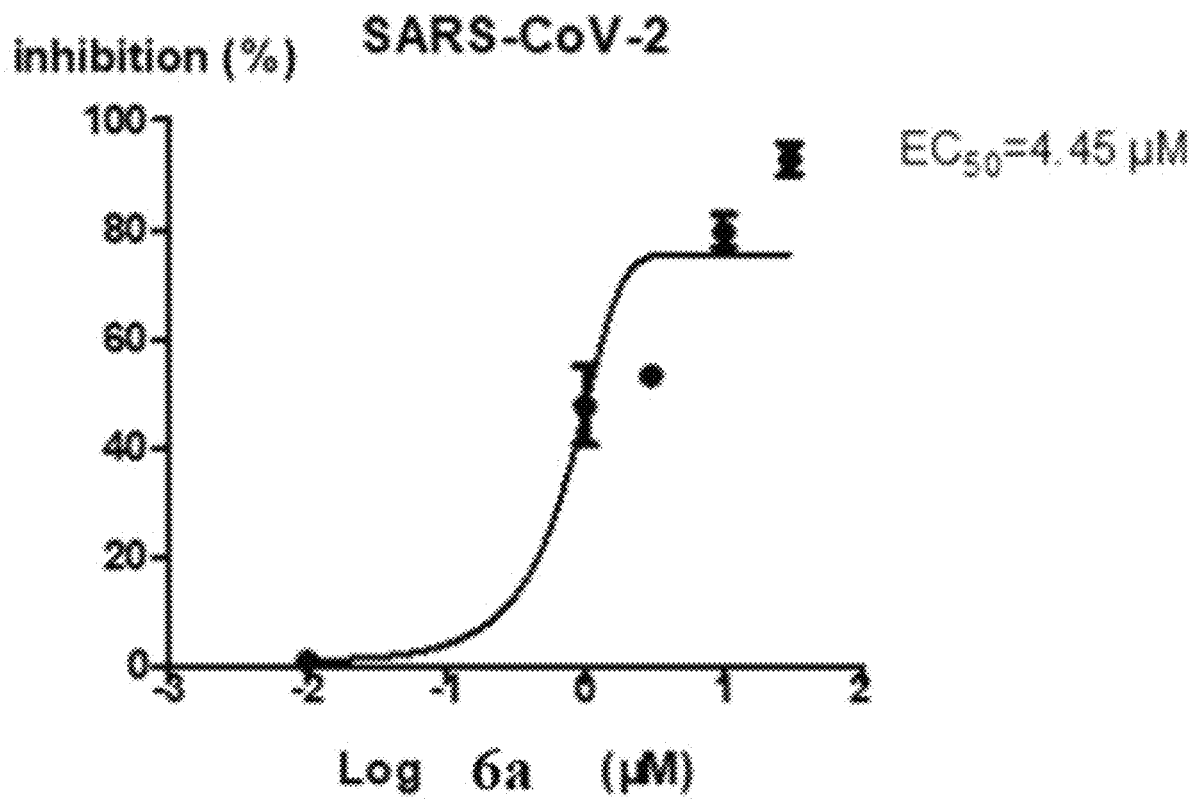
FIG. 3 shows the results of determining the $IC_{50}$ of the compound 6a provided in an example of the present invention in Vero E6 cells for inhibiting the replication of COVID-19 viruses.

Experimental results: As shown in FIG. 2, in the Vero cells infected with COVID-19 virus, the compounds 6a, 6b, and 6c at concentrations of 30 μM and 10 μM, all show strong antiviral effects. Among them, the compound 6a has the most potent ability to inhibit the virus replication, with an $EC_{50}$ of 4.45 uM, as shown in FIG. 3.

EXAMPLE 10

Preparation of Antiviral Agents or Drugs for the Treatment of Coronavirus Pneumonia with Bromophenol-pyrazoline Compounds The bromophenol-pyrazoline compounds prepared in Examples 1-7 can be prepared into an antiviral preparation that inhibits the virus replication, or used as an active ingredient to prepare a pharmaceutical composition in combination with a pharmaceutically acceptable carrier.

In the aforementioned antiviral preparations or pharmaceutical compositions, the active ingredient can be a single compound or a mixture of any two or more of the aforementioned compounds. They can be made into any dosage form as needed.

The invention claimed is:

1. A bromophenol-pyrazoline compound of following formula:

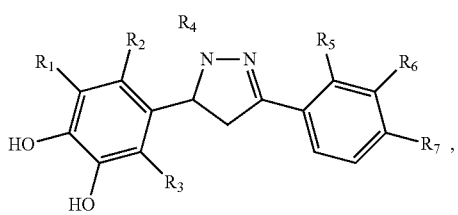

wherein $R_1$, $R_2$ and $R_3$ each are independently selected from the group consisting of H and Br;

$R_4$ is selected from the group consisting of H, CHO, $COCH_3$, $COCH_2CH_3$, $COCH_2CH_2CH_3$, $COOCH_3$, $COOCH_2CH_3$, phenyl (Ph), $CH_2Ph$, $CONH_2$, $CSNH_2$,

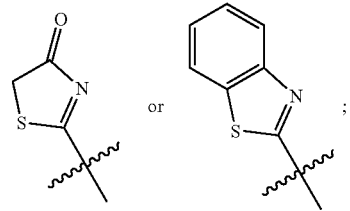 [SMILES: *C1=NC(=O)CS1 ; *c1nc2ccccc2s1]

$R_5$, $R_6$ and $R_7$ each are independently selected from the group consisting of H, Br, $NO_2$, OH, $CH_3$, $OCH_3$ and

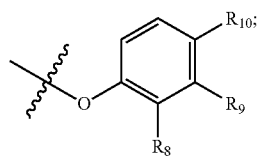

and
one of $R_5$, $R_6$ and $R_7$ is

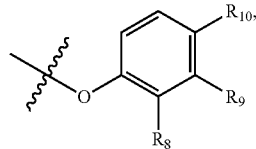

wherein $R_8$, $R_9$ and $R_{10}$ each are independently selected from the group consisting of H, methyl, ethyl, methoxy, ethoxy, isopropyl and t-butyl.

2. The bromophenol-pyrazoline compound of claim 1, wherein the bromophenol-pyrazoline compound is selected from the group consisting of:

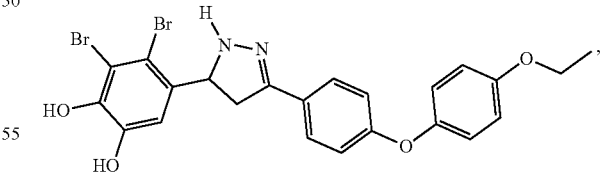

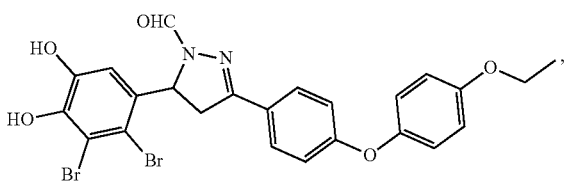

-continued

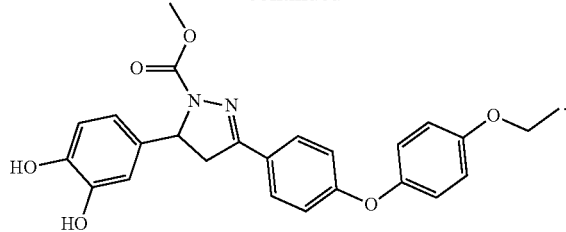

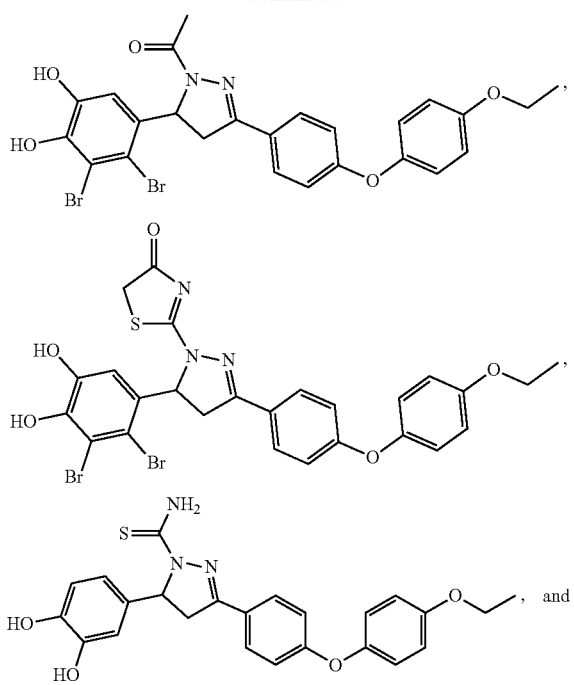

3. A drug composition, comprising an effective dose of the bromophenol-pyrazoline compound of claim 1, and a pharmaceutically acceptable carrier.

4. A drug composition, comprising an effective dose of the bromophenol-pyrazoline compound of claim 2, and a pharmaceutically acceptable carrier.

5. A method of treating coronavirus pneumonia in a subject, comprising:
   administering an therapeutically effective amount of the bromophenol-pyrazoline compound of claim 1 to the subject in need thereof.

6. A method of treating coronavirus pneumonia in a subject, comprising:
   administering an therapeutically effective amount of the bromophenol-pyrazoline compound of claim 2 to the subject in need thereof.

* * * * *